United States Patent [19]
Duronio et al.

[11] Patent Number: 5,504,008
[45] Date of Patent: Apr. 2, 1996

[54] METHOD FOR PROTEIN N-MYRISTOYLATION

[75] Inventors: Robert J. Duronio, St. Louis; Peter O. Olins, Ballwin; Jeffrey I. Gordon, St. Louis, all of Mo.

[73] Assignee: Washington University, St. Louis, Mo.

[21] Appl. No.: 274,606

[22] Filed: Jul. 13, 1994

Related U.S. Application Data

[63] Continuation of Ser. No. 485,103, Feb. 26, 1990, abandoned.

[51] Int. Cl.$^6$ ............ C12N 15/70; C12N 15/68; C12N 15/54; C12N 9/10
[52] U.S. Cl. ............ 435/320.1; 435/69.1; 435/193; 435/252.33; 536/23.2; 935/10; 935/29; 935/73
[58] Field of Search ............ 435/193, 252.33, 435/320.1; 536/23.2

[56] References Cited

U.S. PATENT DOCUMENTS

| | | | |
|---|---|---|---|
| 4,709,012 | 11/1987 | Adams et al. | 530/328 |
| 4,740,588 | 4/1988 | Adams et al. | 530/328 |
| 4,778,877 | 10/1988 | Adams et al. | 530/328 |
| 4,778,878 | 10/1988 | Adams et al. | 530/328 |

OTHER PUBLICATIONS

Rosenwasser, T. A., et al., 1990, The Journal of Biological Chemistry, 265(22):13066–13073
Kishore, N. S., et al., 1991, The Journal of Biological Chemistry, 266(14):8835–8855.
Radnick, D. A., et al., 1992, The Journal of Biological Chemistry, 267(33):23852–23861.
Duronio, R. J., et al., 1992, Proceedings of the National Academy of Sciences, U.S.A., 89:4129–4133.
Ray, S., et al., 1992, Proceedings of the National Academy of Sciences, U.S.A., 89:5705–5709.
Yonomoto, W., et al., 1993, The Journal of Biological Chemistry, 268(25):18626–18632.
Duronio, R. J., et al., 1990, Methods—A Companion to Methods in Enzymology, 3(1):253–263.
Rudnick, D. A., et al., 1990, The Journal of Biological Chemistry, 265(22):13370–13378.
Lodge, J. K., et al., 1994, The Journal of Biological Chemistry, 269(4):2996–3009.
Duronio, R. J. 1991, The Journal of Biological Chemistry, 266(16):10498–10504.
Duronio, R. J., et al., 1990, Proceedings of the National Academy of Sciences, U.S.A., 87:1506–1510.
Blackshear, P. J., et al., 1992, The Journal of Biological Chemistry, 267(19):13540–13546.
Towler & Glaser, Biochemistry 25, 878–84 (1986).
Towler & Glaser, Proc. Natl. Acad. Sci. USA 83, 2812–2816 (1986).
Towler et al., Proc. Natl. Acad. Sci. USA 84, 2708–2712 (1987).
Towler et al., J. Biol. Chem. 262, 1030–1036 (1987).
Towler et al., Ann. Rev. Biochem. 57, 69–99 (1988).
Heuckeroth et al., Proc. Natl. Acad. Sci. USA 86, 8795–8799 (1989).

(List continued on next page.)

*Primary Examiner*—Robert A. Wax
*Assistant Examiner*—William W. Moore
*Attorney, Agent, or Firm*—Scott J. Meyer

[57] ABSTRACT

There is disclosed a method for providing for the coexpression of N-myristoyltransferase and a protein substrate for said N-myristoyltransferase in *E. coli* comprising introducing into *E. coli* a dual plasmid system comprising (A) the isopropyl-$\beta$-D-thiogalactopyranoside-inducible tac promoter, the g10-L ribosome binding site, a NMT gene, the kanamycin resistance gene and the p15A origin of replication in operable sequence and (B) the recA promoter, the g10-L ribosome binding site, a mammalian gene, the ampicillin resistance gene and the Col E1 origin of replication in operable sequence. This allows production of mammalian N-myristoylproteins or proteins containing covalently linked analogs of myristate with altered physical-chemical properties.

4 Claims, 4 Drawing Sheets

OTHER PUBLICATIONS

Heuckeroth and Gordon, Proc. Natl. Acad. Sci. USA 86, 5262–5266 (1989).
Duronio et al., Science, 243, 796–800 (1989).
Olins et al., Gene 73, 227–235 (1988).
Olins and Rangwals, J. Biol. Chem. 264, 16973–16976 (1989).
Horii et al., Proc. Natl. Acad. Sci. USA 77, 313–317 (1980).
Uhler et al., Proc. Natl. Acad. Sci. USA 83, 1300–1304 (1986).

METHOD FOR PROTEIN N-MYRISTOYLATION

This is a CONTINUATION of application Ser. No. 07/485,103, filed Feb. 26, 1990, now abandoned.

BACKGROUND OF THE INVENTION

This invention relates to a method for producing N-myristoylated protein and, more particularly, to the co-expression of N-myristoyltransferase (NMT) and its protein substrates in *E. coli*.

Fatty acid acylation of specific eukaryotic proteins is a well established process which can conveniently be divided into two categories. On the one hand, palmitate (C16:0) is linked to membrane proteins via ester or thioester linkage post-translationally.

On the other hand, it is known that myristate (C14:0) becomes covalently bound to soluble and membrane proteins via amide linkage. This is believed to be a co-translational event. In the N-myristoylated proteins, amino-terminal glycine residues are known to be the site of acylation. Myristoyl CoA: protein N-myristoyltransferase (NMT, E.C. 2.3.1.97) catalyzes this co-translational modification. The NMT structural gene (NMT1) has recently been cloned from *Saccharomyces cerevisiae*. See Duronio et al., *Science* 243, 796–800 (1989). This gene encodes a polypeptide of 455 amino acids ($M_r$=52,837).

A variety of viral and cellular proteins have been shown to be thus modified by the covalent attachment of myristate linked through an amide bond to glycine at their amino termini. Such modification is essential for the full expression of the biological function of some N-myristoylated proteins. An example of a most thoroughly studied myristoylated protein is the transforming protein of Rous sarcoma virus, $p60^{v-src}$. Without the covalent attachment of myristate to its N-terminal glycine, the protein cannot transform cells even though its tyrosine kinase activity remains intact.

The myristoylation reaction can be represented as follows:

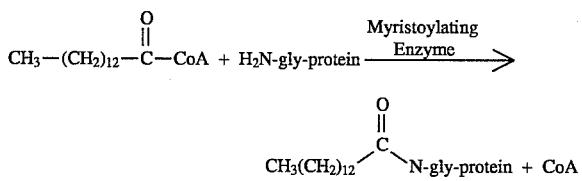

Further background information on the above protein fatty acid acylation can be had by reference to the following series of articles by scientists associated with the Washington University School of Medicine:

Towler and Glaser, *Biochemistry* 25, 878–84 (1986);

Towler and Glaser, *Proc. Natl. Acad. Sci. USA* 83, 2812–2816 (1986);

Towler et al., *Proc. Natl. Acad. Sci. USA* 84, 2708–2712 (1987);

Towler et al., *J. Biol. Chem.* 262, 1030–1036 (1987);

Towler et al., *Ann. Rev. Biochem.* 57, 69–99 (1988);

Heuckeroth et al., *Proc. Natl. Acad. Sci. USA* 85, 8795–8799 (1988); and

Heuckeroth and Gordon, *Proc. Natl. Acad. Sci. USA* 86, 5262–5266 (1989).

Unique synthetic peptides having relatively short amino acid sequences which are useful as substrates of myristoylating enzymes are described in U.S. Pat. Nos. 4,740,588 and 4,778,878. Examples of such peptides are:

Gly-Asn-Ala-Ala-Ala-Ala-Arg-Arg and

Gly-Asn-Ala-Ala-Ser-Tyr-Arg-Arg.

Certain other unique synthetic peptides are inhibitors of myristoylating enzymes as described in U.S. Pat. Nos. 4,709,012 and 4,778,877.

In applications Ser. No. 07/208,192, filed Jun. 16, 1988, now abandoned, Ser. No. 07/402,094 filed Sep. 1, 1989, now U.S. Pat. No. 5,073,571, and Ser. No. 07/478,298 filed Feb. 9, 1990, now U.S. Pat. No. 5,082,967, novel fatty acid analog substrates of myristoylating enzymes are described which have potential use as antiviral, antifungal and antineoplastic agents. These substrate compounds are mono- and diheteroatom-substituted fatty acid analogs in which the heteroatoms are oxygen and/or sulfur which replace methylene ($-CH_2-$) groups in carbon positions 4 to 13 in the fatty acid chain of $C_{13}-C_{14}$ fatty acids. Examples of such fatty acid analogs are:

11-oxamyristic acid and 13-oxamyristic acid.

The CoA ester of these fatty acid analogs are substrates for NMT and are selectively transferred to subsets of cellular or viral N-myristoylproteins where they can alter protein function.

BRIEF DESCRIPTION OF THE INVENTION

In accordance with the present invention a novel method for the co-expression of N-myristoyltransferase (NMT, E.C. 2.3.1.97) and its protein substrates in *E. coli* is provided. Using a dual plasmid system, N-myristoylation of a mammalian protein can be reconstituted in *E. coli* by simultaneous expression of a NMT gene and a cDNA encoding the protein.

The novel method of the present invention provides a new system for studying the substrate requirements and biological effects of protein N-myristoylation, as well as NMT structure/activity relationships. To illustrate the invention, expression of the yeast NMT1 gene in *E. coli*, a bacterium which has no endogenous NMT activity, results in production of the intact 53 kDa NMT polypeptide as well as a truncated polypeptide derived from proteolytic removal of its NH2-terminal 39 amino acids. Each *E. coli*-synthesized NMT species has fatty acid and peptide substrate specificities that are indistinguishable from those of NMT recovered from *S. cerevisiae* as judged by an in vitro assay of enzyme activity, suggesting that the $NH_2$-terminal domain of this enzyme is not required for its catalytic activity. Using a dual plasmid system, N-myristoylation of a mammalian protein was reconstituted in *E. coli* by simultaneous expression of the yeast NMT1 gene and a murine cDNA encoding the catalytic (C) subunit of cAMP-dependent protein kinase (PK-A). Metabolic labeling studies indicated that the fatty acid specificity of N-myristoylation was preserved in this system. [$^3$H]Myristic acid but not [$^3$H]palmitate was efficiently linked to the $Gly^1$ residue of the C-subunit.

It was also found in accordance with the present invention that [$^3$H]10-(propoxy)decanoic acid, a heteroatom containing analog of myristic acid with reduced hydrophobicity but similar chain length, was an effective alternative substrate for NMT that could be incorporated into the C-subunit of PK-A.

Such heteroatom containing analogs of myristic acid have recently been shown in copending application Ser. No. 07/402,094, filed Sep. 1, 1989, to inhibit replication of certain retroviruses that depend upon linkage of a myristoyl group to their gag polyprotein precursors (e.g. the Pr55$^{gag}$ of human immunodeficiency virus 1; HIV-I).

A major advantage of the bacterial system as defined herein over eukaryotic systems is the absence of endogenous NMT and substrates, providing a more straightforward way of preparing myristoylated, analog substituted, and non-myristoylated forms of a given protein for comparison of their structural and functional properties. The present method facilitates screening of enzyme inhibitors as well as alternative NMT substrates, such as heteroatom containing analogs, for their ability to be incorporated into a specific target protein. Finally, the present method also is useful for recapitulating other eukaryotic protein modifications in E. coli so that structure/activity relationships of modifying enzymes and their substrates can be more readily assessed.

For production of yeast NMT1 in E. coli, the NMT1 gene can be cloned into a suitable plasmid expression vector such as, e.g., pMON5840. This plasmid is a variant of pMON5515 which, in addition to an irrelevant sequence, contains the recA promoter ($P_{rec}A$) and the ribosome-binding site, derived from bacteriophage T7 phage gene 10 leader RNA (g10-L RBS), and is suitable for enhanced expression of foreign genes in E. coli, as further described by Olins et al., Gene 73, 227–235 (1988); Olins and Rangwala, J. Biol. Chem. 264, 16973–16976 (1989). The recA promoter in pMON5840 is derived as the HpaII fragment and corresponds to nucleotides 63-210 of the sequence published by Horii et al., Proc. Natl. Acad. Sci. USA 77, 313–317 (1980). The yeast NMT1 gene can be ligated into the parent vector which can then be used for expression of the NMT by conventional procedures.

In particular, the yeast NMT1 gene is placed downstream of the g10-L by engineering an NcoI site at its initiator Met codon and subcloning the DNA into pMON5840. NMT transcription is thereby put under the control of the E. coli recA promoter located upstream of the g10-L sequence in pMON5840. E. coli JM101 cells carrying this recombinant plasmid are grown to mid-log phase and then treated with naladixic acid to induce the recA promoter.

Using the foregoing plasmid system, NMT was subsequently purified ~750-fold by sequential ammonium sulfate fractionation, DEAE-Sepharose® CL-6B and CoA-agarose affinity chromatography of cell lysates. By using a coupled in vitro assay for NMT activity [Towler and Glaser, Proc. Natl. Acad. Sci. USA 83, 2812–2816 (1986)], it was determined that the partially purified E. coli-derived NMT displayed $K_m$ and $V_{max}$ values for various peptide substrates which were nearly identical to those of a partially purified NMT preparation from yeast.

A dual plasmid system was used to coexpress in E. coli the yeast NMT1 gene and a cDNA (Cα) encoding the murine Cα catalytic subunit of cAMP-dependent protein kinase (PK-A) described by Uhler et al., Proc. Natl. Acad. Sci. USA 83, 1300–1304 (1986). One plasmid was constructed by cloning the 1.9 kb NcoI-HindIII NMT1 fragment in pMON5839, which is a derivative of pACY177 containing the kanamycin resistance gene and the p15A origin of replication. Another plasmid was constructed by cloning a 1.8 kb NdeI-KpnI Cα cDNA in pMON2670 containing the ampicillin resistance gene and the ColE1 origin of replication.

Co-expression of NMT and its protein substrates in E. coli thus can facilitate analysis of NMT structure/activity relationships, help identify structural features of its protein substrates that are necessary for N-myristoylation, and provide insights about the role of the myristoyl moiety in the function of individual N-myristoyl proteins. The effect of modifying specific N-myristoyl proteins with heteroatom-containing analogs of myristate can now be directly assessed by comparative studies of E. coli-synthesized nonacylated, myristoylated, and analog substituted species. Mutant strains of E. coli deficient in the metabolism of fatty acids [Silbert, Ann. Rev. Biochem. 44, 315–339 (1975); Nunn et al., J. Biol. Chem. 261, 167–171 (1986)] can be particularly useful in these studies by improving the ability to deliver exogenous fatty acids and their analogs to the acylation apparatus. Finally, given the observation [Heuckeroth et al., Proc. Natl. Acad. Sci. USA 85, 8795–8799 (1988)] that acyl-CoA binding to NMT affects the enzyme's affinity for various peptide substrates, the co-expression of NMT and its protein substrates in E. coli can provide a good functional assay for screening the relative efficiency of incorporation of different analogs into a given target protein. In this sense, the N-myristoylation system defined herein may aid in the identification of useful anti-tumor or anti-viral drugs.

The foregoing parental plasmid vectors, pMON2670 and pMON5840, each carried in JM101 E. coli, are on deposit with the American Type Culture Collection, Rockville, Md., under accession numbers ATCC 68218 and ATCC 68220, respectively.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention taken in conjunction with the appended drawings in which:

Figure 1A:
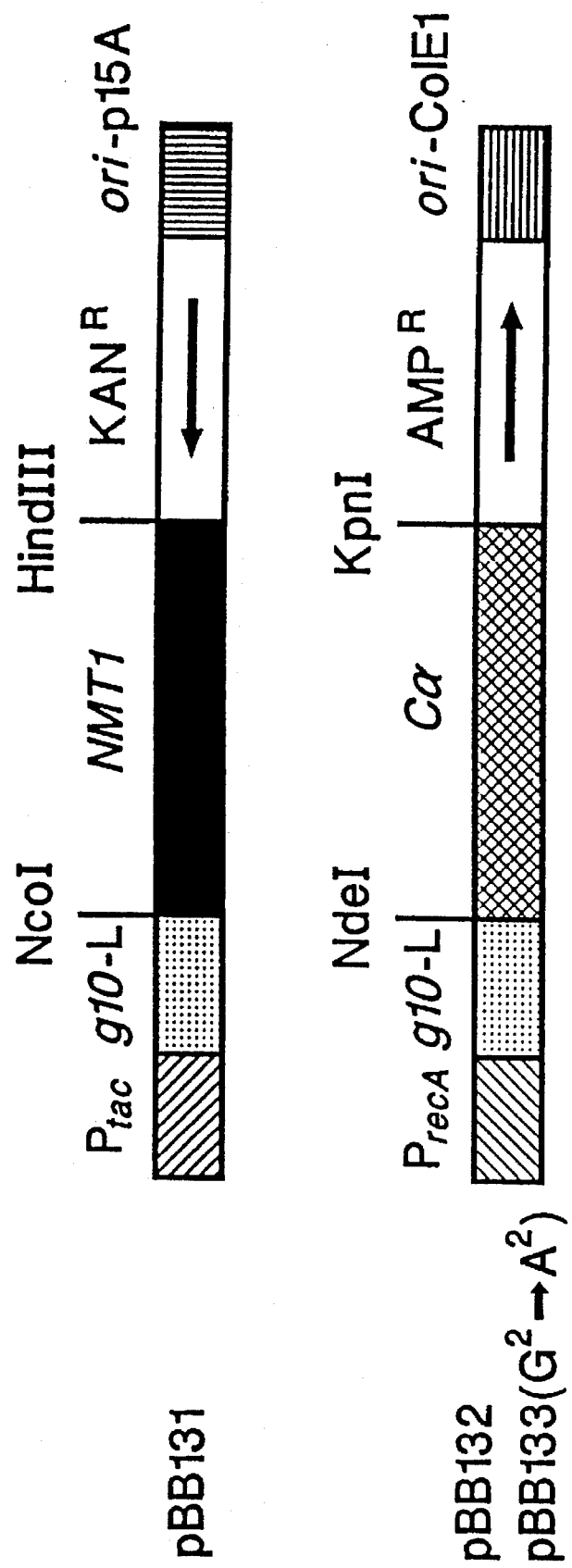
FIG. 1A (Panel A) is a schematic representation of plasmid constructs used to express the NMT1 and Cα DNAs in E. coli.
Figures 1B, 1C, 1D:
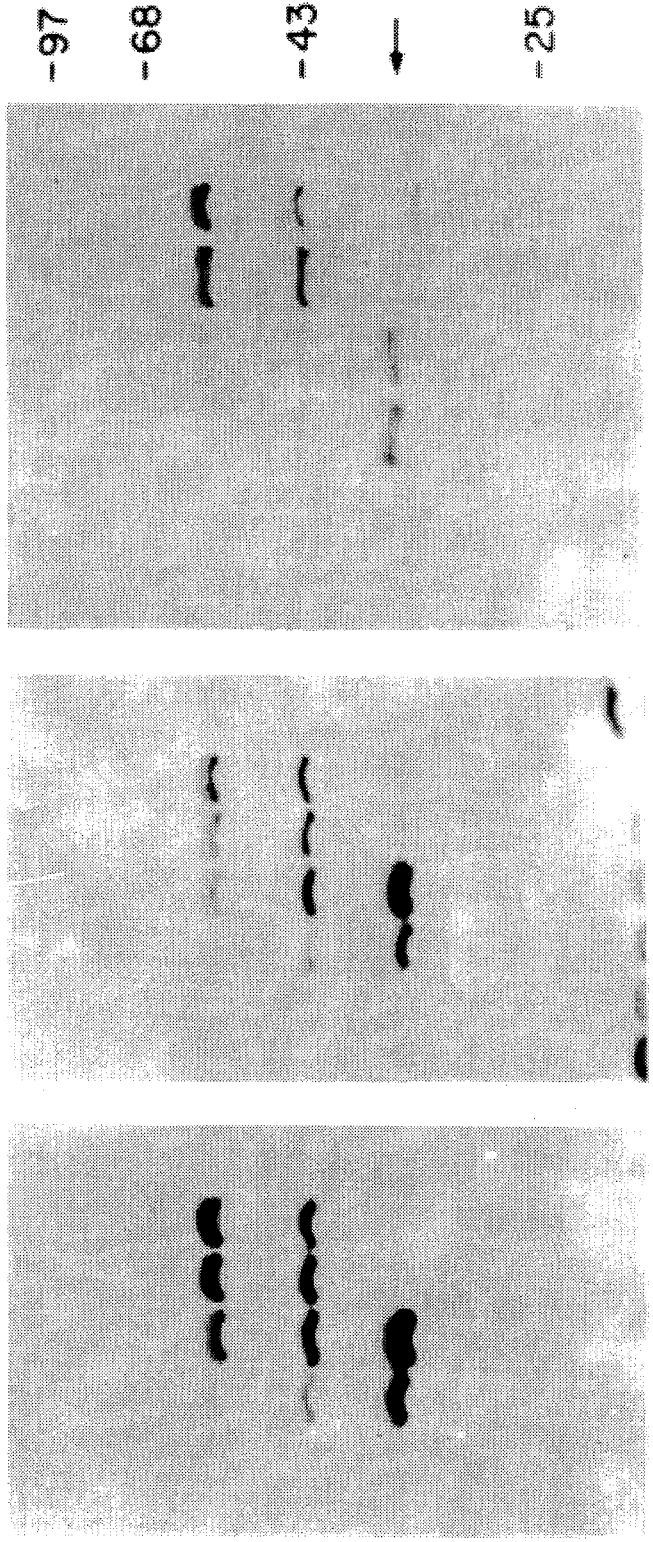
FIG. 1 shows in five panels, A, B, C, D and E, the N-myristoylation of the murine cAMP dependent protein kinase catalytic (C) subunit synthesized in E. coli in an illustrative embodiment of the invention.

FIGS. 1B, 1C and 1D (Panels B, C and D) show gel patterns in which lysates were prepared from E. coli transformants containing different combinations of plasmids after labeling with exogenously added [$^3$H]myristate (panel B), [$^3$H]palmitate (panel C) or [$^3$H]10-(propoxy)decanoate (panel D). [$^3$H]Lysate proteins were then subjected to SDS-PAGE and fluorography. The arrow indicates the position of migration of purified mouse C-subunit. The fluorographic exposure time for the gels shown in panels B and C was 4 days while the gel shown in panel D was exposed for 15 days. Lane 1, E. coli strain JM101 without plasmids; lane 2, JM101 plus parental vectors; lane 3, JM101 plus recombinant NMT1- and Cα-containing plasmids, without induction; lane 4, JM101 plus NMT1 and Cα plasmids after induction; lane 5, JM101 plus NMT1 and mutant Ala$^2$ Cα plasmids after induction; lane 6, JM101 plus NMT1 and parental vector lacking Cα insert after induction; lane 7, JM101 plus Cα and parental vector lacking NMT1 insert after induction.

Figure 1E:
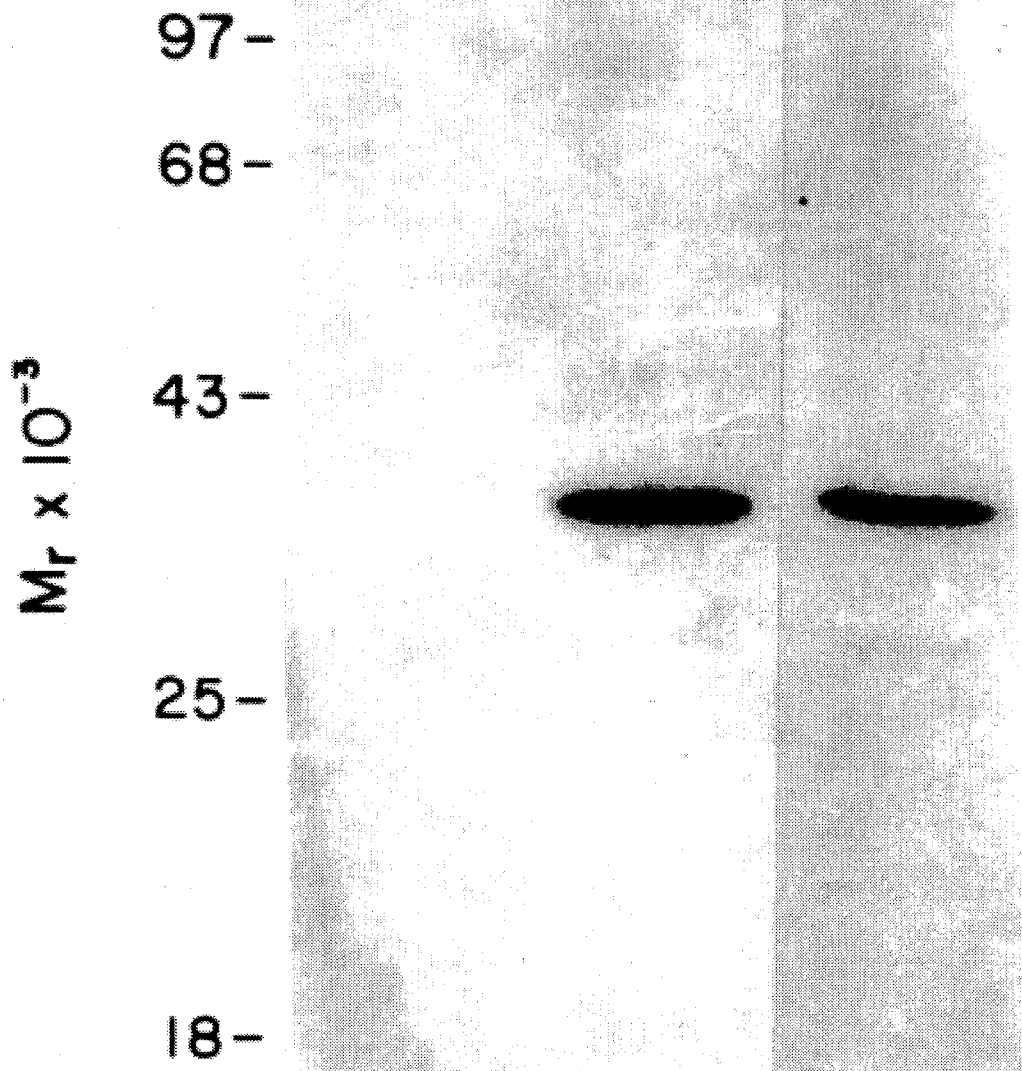

FIG. 1E (Panel E) shows Western blot analysis of E. coli lysates containing wild type Gly$^2$-C-subunit or mutant Ala$^2$-C-subunit. The blots were probed with a rabbit anti-mouse C-subunit sera.

Figure 2:
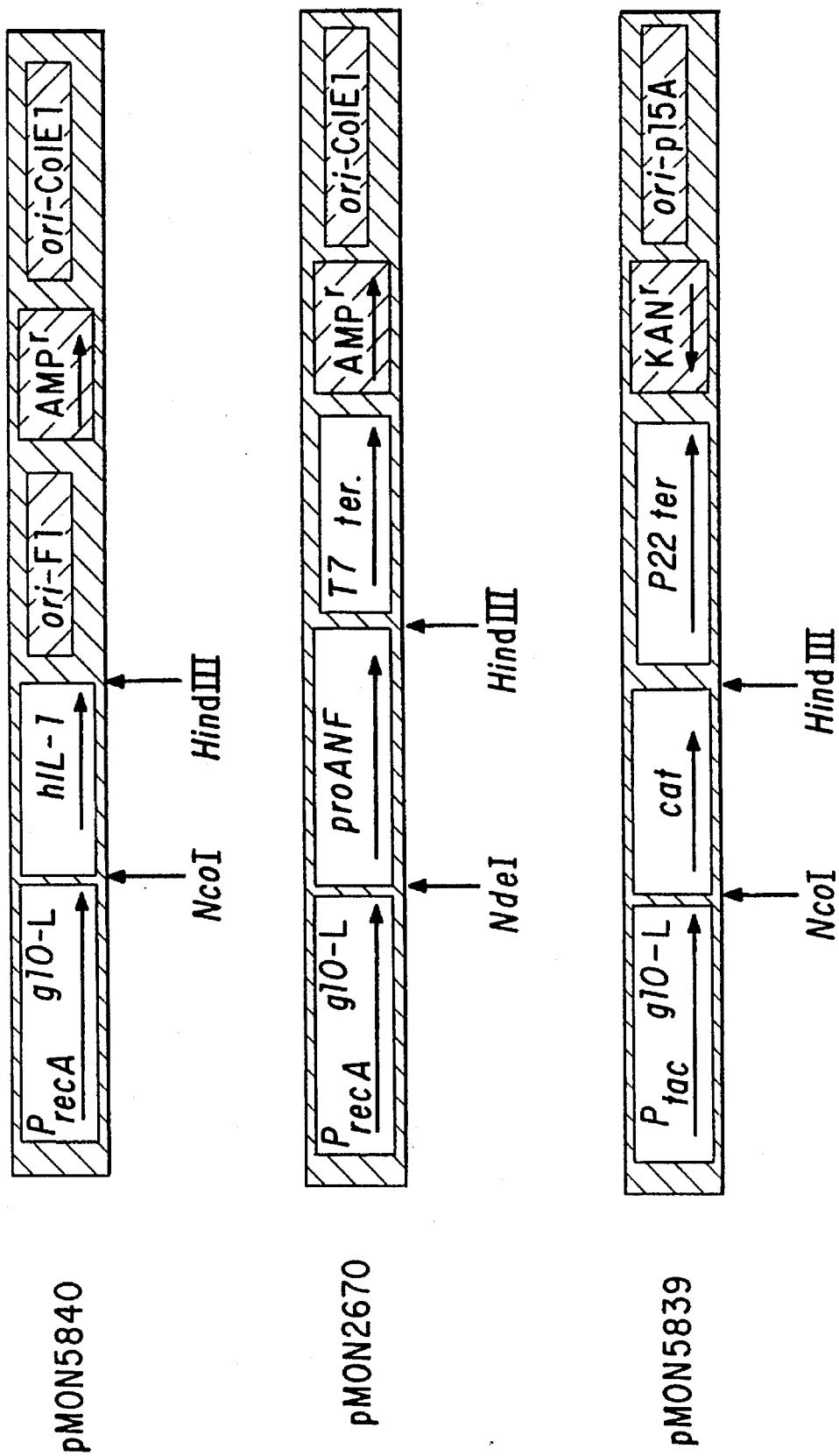

FIG. 2 is a schematic representation of parental plasmid vectors, pMON5840, pMON2670 and pMON5839, used for construction of expression plasmids for the NMT1 and Cα genes described in FIG. 1.

In order to illustrate the invention in greater detail, the following exemplary laboratory preparative work was carried out.

EXAMPLES

MATERIALS AND METHODS

Parental expression vectors used for production of NMT-1 and Cα in *E. coli*. Two plasmids carrying the ColE1 origin of replication were used in this example, pMON2670 and pMON5840, as illustrated schematically in FIG. 2. *E. coli* JM101 strains harboring these plasmids have been deposited with the ATCC, and are available under accession numbers ATCC 68218 and ATCC 68220, respectively. Briefly, the plasmids are based on plasmid pMON5515 described by Olins et al., *Gene* 73, 227–235 (1988), and consist of an ampicillin resistance marker (AMP$^r$) and ColE1 replicon (ori-ColE1), the nalidixic acid-inducible *E. coli* recA promoter and the g10-L ribosome binding site. In addition, pMON2670 carries a T7 transcription terminator (T7 ter.), while pMON5840 contains the single-stranded origin of replication (ori-F1) from F1 phage [Dente et al, *Nucleic Acids Res.* 11, 1645 (1983)], which also acts as a transcription terminator. The two plasmids also contain irrelevant coding regions (for pMON2670, a portion of the human proANF gene, proANF; for pMON5840, a portion of the human interleukin-1 gene, hIL-1) downstream of the G10-1 ribosome binding site. Unique NcoI, NdeI and HindIII restriction sites permitted the simple removal of the irrelevant coding regions.

For dual-plasmid expression of NMT1 in *E. coli* a plasmid vector based on pACYC177 [Chang and Cohen, *J. Bacteriol.* 134, 1141–1156 (1978)] was used, as illustrated schematically in FIG. 2. An *E. coli* JM101 strain harboring this plasmid, namely plasmid pMON5839, contains the p15A origin of replication (orip15A) and a kanamycin resistance gene (KAN$^r$), as a selectable marker. The plasmid contains the inducible tac promoter ($P_{tac}$) [De Boer et al., *DNA* 2, 213–235 (1988)] and a transcription terminator derived from phage P22 sequences (P22 ter.) The plasmid also contains an irrelevant coding region (a bacterial chloramphenicol acetyl transferase gene, cat) downstream of the g10-L ribosome binding site, which could be simply removed by cleavage with NcoI and HindIII.

Expression of *S. cerevisiae* NMT in *E. coli*. A 780 base pair region (nucleotides 213 to 993) of the 2.1 kilobase (kb) Bam HI-HindIII *S. cerevisiae* genomic NMT1 fragment [Duronio et al., *Science* 245, 796–800 (1989)] was amplified using the polymerase chain reaction [Saiki et al., *Science* 239, 487–491 (1988)] and a mutagenic oligonucleotide (5'CGGTAGTAAACGGA-TCCATACCATG GCAGAAGAGGATAAAGCGAAAAAAT3'). This allowed introduction of an NcoI restriction enzyme site at the initiator ATG codon of NMT1. The new NcoI site also changed codon two of NMT1 from a serine to an alanine. Amplification products were subcloned back into pBB105 (Duronio et al., supra.) to generate the altered NMT1 allele. The NcoI site allowed linking of the NMT1 gene to the *E. coli* recA promoter [Horii et al., *Proc. Natl. Acad. Sci. USA* 77, 313–317 (1980)] and a translational enhancer element obtained from phage T7 (g10-L in FIG. 1A). This was accomplished by ligating the newly generated 1.9 kb NcoI-HindIII fragment into NcoI-HindIII digested pMON5840, described above. The resulting plasmid (pBB125) was used to transform *E. coli* strain JM101 [Messing, *Recombinant DNA Tech. Bull.* 2, 45–48 (1979)]. Transformants were shaken at 37° C. in LB broth+100 µg/ml ampicillin to an OD$_{600}$ of 1.0. The recA promoter was induced by adding nalidixic acid to a final concentration of 50 µg/ml [Feinstein et al., *Nuc. Acids Res.* 11, 2927–2941 (1983)]. Following a 15–20 min incubation at 37° C., cells were harvested by centrifugation and broken under pressure (2000 pounds/ square inch) with a Power Laboratory Press (American Instrument Co.). NMT species were purified as described below.

Plasmids for coexpression of NMT1 and Cα in *E. coli*. pBB131 was constructed by cloning the 1.9 kb Nco I-Hind III NMT1 fragment into pMON5839, a derivative of pACYC177 [Chang and Cohen, *J. Bact.* 134, 1141–1156 (1978)]. Cα cDNAs encoding the catalytic subunit of PK-A [Uhler et al., *Proc. Natl. Acad. Sci. USA* 83, 1300–1304 (1986)] were cloned as 1.8 kb Nde I-Kpn I fragments into pMON2670, described above and by Li et al., *J. Biol. Chem.* 262, 13773–13779 (1987). pBB132 contains the wild type Cα cDNA (from G. Stanley McKnight), which specifies a Gly at position 2 of its primary translation product (the initiator Met occupies position 1). A mutant Cα cDNA with an Ala at position 2 was made by oligonucleotide site-directed mutagenesis using a modified procedure of Zoller and Smith, *Nuc. Acids Res.* 10, 6487–6500 (1982). Uracil-containing single strand template was prepared from the phagemid pUCl19/Cα in RZ1032 cells [Kunkel, *Proc. Natl. Acad. Sci. USA* 32, 488–492 (1985)], and Gly$^2$→Ala$^2$ mutagenesis was performed with the oligomer 5'-CATATG GCCAACGCCGCC-3'. The mutation was confirmed by dideoxynucleotide sequencing [Sanger et al., *Proc. Natl. Acad. Sci. USA* 74, 5463–5467 (1977)]. pBB131 (NMT1) and pBB132 (Gly$^2$-Cα) or pBB133 (Ala$^2$-Cα) were used to transform *E. coli* strain JM101. Restriction analysis of plasmid DNA confirmed the identity of constructs within ampicillin/kanamycin resistant *E. coli* double transformants.

[$^3$H]Fatty acid labeling of PK-A C-subunit produced in *E. coli*. Four ml cultures of the double transformants were shaken at 37° C. to an OD$_{600}$ of 0.5 in LB broth+100 µg/ml ampicillin and 100 µg/ml kanamycin sulfate. Isopropyl-β-D-thiogalactopyranoside (IPTG) was then added to a final concentration of 1 mM to induce NMT production (see Results, below). When the cultures reached OD$_{600}$=1.0 (approximately 40 min later), nalidixic acid was added to a final concentration of 50 µg/ml to induce C-subunit production (see Results, below). [$^3$H]Myristate (New England Nuclear; 39.3 Ci/mmol, 113 µCi added per ml of culture), [$^3$H]palmitate (New England Nuclear; 30 Ci/mmol, 143 µCi/ml), or [$^3$H]10-(propoxy)decanoate [Heuckeroth and Gordon, *Proc. Natl. Acad. Sci. USA* 86, 5262–5266 (1989)] (31.7 Ci/mmol, 800 µCi/ml) was added simultaneously with the nalidixic acid. Cultures were shaken for an additional 20 min at 37° C. and the cells were harvested by centrifugation. Lysates were prepared by boiling *E. coli* contained in the pellet for 10 min in 40 µL of a solution of 125 mM Tris, pH 8.0, 4% SDS, 20% glycerol, 10% β-mercaptoethanol, and 0.2M dithiothreitol. Cell debris was removed by centrifugation and 15 µl aliquots of the supernatant were subjected to SDS-PAGE [Laemmli, *Nature* 227, 680–685 (1970)] and subsequent fluorography using EN$^3$HANCE (New England Nuclear) autoradiography enhancer. For Western blot analyses, 50 µg of reduced and denatured lysate proteins, prepared from unlabeled *E. coli* producing Gly$^2$-C-subunit or Ala$^2$-C-subunit, were separated by SDS-PAGE, electroblotted onto nitrocellulose [Burnette, *Anal. Biochem.* 112, 195–230 (1981)], and the filters probed with polyclonal, monospecific rabbit antisera raised against purified mouse C-subunit. Antigen-antibody complexes were visualized with $^{125}$I-protein A [Burnette, supra.].

In vitro assay system for NMT activity. To assess the peptide and acyl-CoA substrate specificities of *E. coli*-derived *S. cerevisiae* NMT, crude lysates or partially purified enzyme preparations were added to a coupled in vitro assay system [Towler and Glaser, *Proc. Natl. Acad. Sci. USA* 83, 2812–2816 (1986)]. The first step of this assay involves enzymatic conversion of radiolabeled fatty acids to their CoA thioesters by Pseudomonas acyl-CoA ligase. This ligase is largely nonspecific for fatty acid substrates [Shimizu et al., *Anal. Biochem.* 107, 193–198 (1980)]. Octapeptide substrates and NMT were then added to produce acylpeptides. Acylpeptides were purified from the reaction mixture by trichloroacetic acid/methanol precipitation and $C_{18}$ reverse phase HPLC using a linear gradient of acetonitrile in water [Towler and Glaser, *Proc. Natl. Acad. Sci. USA* 83, 2812–2816 (1986)].

RESULTS

*S. cerevisiae* NMT Produced in *E. coli* has a Substrate Specificity Similar to that of the Authentic Yeast Enzyme. The *S. cerevisiae* NMT1 gene encodes a protein of 455 amino acids with a calculated $M_r$ of 52,837 that is essential for vegetative cell growth [Duronio et al., *Science* 245, 796–800 (1989)]. The polypeptide has no identifiable significant primary sequence homology with any protein entered in currently available databases (Duronio et al., Ibid.) A six step 11,000 fold purification involving the use of 4 different chromatographic matrices was required to obtain an apparently homogenous preparation of enzyme from this yeast [Towler et al., *Proc. Natl. Acad. Sci. USA* 84, 2708–2712 (1987)]. *E. coli* lysates contain no detectable NMT activity as judged by a sensitive in vitro assay [Towler and Glaser, *Proc. Natl. Acad. Sci. USA* 83, 2812–2816 (1986)] for the enzyme. Thus, expression of yeast NMT in this prokaryote offers an opportunity to obtain large quantities of wild type (or mutant) protein whose activity could be measured in the absence of any endogenous myristoyltransferases.

The expression of *S. cerevisiae* NMT in *E. coli* was achieved using pMON plasmid vectors. These vectors contain inducible promoters fused to a translational "enhancer" derived from the gene 10 leader region (g10-L) of bacteriophage T7 [Olins et al., *Gene* 73, 227–235 (1988)]. The yeast NMT1 gene was placed immediately downstream of the g10-L by engineering an Nco I site at its initiator Met codon and subcloning the DNA into pMON5840. NMT1 transcription was thereby put under the control of the *E. coli* recA promoter [Horii et al., supra., Olins et al., supra.] located upstream of the g10-L in pMON5840. *E. coli* strain JM101 carrying this recombinant plasmid was grown to mid-log phase and then treated with nalidixic acid to induce the recA promoter [Feinstein et al., *Nuc. Acids Res.* 11, 2927–2941 (1983)]. NMT was subsequently purified ~750-fold by sequential ammonium sulfate fractionation, DEAE-Sepharose CL-6B, and CoA-agarose affinity column chromatography of induced cell lysates [Towler et al., *Proc. Natl. Acad. Sci. USA* 84, 2708–2712 (1987)]. Using the coupled in vitro assay for NMT activity described above, it was determined that the partially purified, *E. coli*-derived yeast NMT displayed $K_m$ and $V_{max}$ values for a variety of octapeptide substrates that were nearly identical to those measured with a partially purified NMT preparation from *S. cerevisiae* [Towler et al., *Proc. Natl. Acad. Sci. USA* 84, 2708–2712 (1987)]. (See Table I, below). For example, introduction of a serine residue at position 5 of a "parental" octapeptide GNAAAARR-NH$_2$ obtained from the NH$_2$-terminal sequence of the C-subunit of PK-A reduced its apparent $K_m$ over 100-fold for both NMT preparations. An NH$_2$-terminal Gly is absolutely required. Substitution of an Ala$^1$ for the Gly$^1$ residue converted the peptide into an inactive substrate (Table I). Addition of an NH$_2$-terminal Met residue also generated an inactive peptide, indicating that yeast NMT partially purified from *E. coli*, like NMT isolated from *S. cerevisiae* (Towler et al., Ibid.), has no associated methionylaminopeptidase activity.

To verify that *E. coli* was producing an intact yeast NMT, proteins eluted from the CoA-agarose column with 100 mM KCl were separated by SDS-PAGE and transferred to a polyvinylidene difluoride membrane (Millipore Corp. ). A ~53 kDa polypeptide corresponding to the mass of the 455 residue yeast NMT [Duronio et al., *Science* 245, 796–800 (1989)] was excised from this membrane and subjected to Edman degradation using an Applied Biosystems Model 470A gas phase sequencer. The NH$_2$-terminal sequence indicated that the 53 kDa polypeptide represented intact yeast NMT.

To obtain a homogenous preparation of the enzyme, *E. coli*-produced NMT was further purified by Mono S fast protein liquid chromatography (FPLC). Coomassie blue staining of SDS-PAGE gels of the 250 mM NaCl eluate of a Mono S column [Towler et al., *Proc. Natl. Acad. Sci. USA* 84, 2708–2712 (1987)] revealed an additional band of ~45 kDa which coeluted with NMT catalytic activity. Edman degradation of the 45 kDa polypeptide revealed that it was missing the NH$_2$-terminal 39 residues of NMT suggesting that portions of the polypeptide chain, such as the Lys$^{39}$-Phe$^{40}$ bond, are susceptible to proteolysis and rapidly lost either during purification or shortly after synthesis in *E. coli*.

The Mono S purified 45 kDa NMT species retained the ability to readily distinguish between myristoyl-CoA and palmitoyl-CoA, and displayed the 100-fold reduction in apparent $K_m$ for Ser$^5$ substituted GNAAAARR-NH$_2$ (Table I). The 45 kDa proteolytic fragment appears to retain a core catalytic domain. The role of the missing 39 amino acids remains unknown, but they may be needed for (essential) interactions of NMT with additional factors within yeast, or for its proper intracellular targeting. Determining whether a genetically engineered 45 kDa NMT could rescue the inviable Nmt$^-$ phenotype of *S. cerevisiae* (Duronio et al., Supra.) should permit one to begin to address these questions. Since *E. coli*-derived NMT has kinetic properties very similar to the yeast-derived NMT, it can also be concluded that the enzyme's peptide and fatty acyl-CoA substrate specificities are not dependent upon either a eukaryotic protein modification or additional yeast specific factors.

Reconstitution of Protein N-Myristoylation in *E. coli*. The data described in Table I indicated that expression of yeast NMT in *E. coli* yielded an enzyme that was properly folded in that its substrate specificities were largely indistinguishable from those of NMT isolated from *S. cerevisiae*. Since there is no endogenous NMT activity in *E. coli*, the results herein raised the possibility that co-expression of yeast NMT and a eukaryotic protein substrate in *E. coli* would permit the reproduction of a protein modification which is apparently exclusively eukaryotic, in a prokaryote.

cAMP dependent protein kinase (PK-A) was one of the earliest protein kinases to be discovered and also one of the best understood biochemically [Taylor, *J. Biol. Chem.* 264, 8445–8446 (1989)]. The kinase is involved in the regulation of cell growth and metabolism, and its catalytic (C) subunit was the first protein shown to be N-myristoylated [Carr et al., *Proc. Natl. Acad. Sci. USA* 79, 6128–6131 (1982)]. Expression of a cDNA (Cα) encoding the murine C-subunit [Uhler et al., supra.) in *E. coli* led to the isolation of a soluble and active form of the protein [Slice and Taylor, *J. Biol. Chem.*, 264, 20940–20946 (1989)] which lacked myristate at the NH$_2$-terminal Gly. Having shown that an octapeptide derived from the NH$_2$-terminus of the murine C-subunit was a good substrate for the intact (and truncated) *E. coil*-derived yeast NMT in vitro (Table I), it was decided to use the C-subunit as an exemplary protein for the in vivo reconstitution tests. The dual plasmid system outlined in FIG. 1A was utilized to coexpress the yeast NMT1 gene and the Cα cDNA. The vectors were designed so each could (i) be simultaneously maintained as a stable episomal plasmid and (ii) support independent induction of transcription of their foreign DNA sequences. Expression of NMT1 was placed under the control of the isopropyl-β-D-thiogalactopyranoside (IPTG)-inducible tac [DeBoer et al., *DNA* 2, 231–235 (1983)] promoter and the g10-L ribosome binding site [Olins et al., *Gene* 73, 227–235 (1988)] contained in a plasmid based on pACYC177 (Messing, supra.). This plasmid includes the p15A origin of replication and a kanamycin resistance gene. Expression of two Cα cDNAs was placed under the control of the recA promoter [Horii et al., supra.) and g10-L present in a plasmid containing the ampicillin resistance gene and ColE1 origin of replication. One of these cDNAs encoded the wild type 40 kDa C-subunit of PK-A (Gly$^2$), while the other produced a variant that had an Ala$^2$ for Gly$^2$ substitution. This mutant C-subunit should not be a substrate for NMT (Table I).

Pairwise combinations of the parental vectors and their NMT1 and Cα containing recombinant derivatives were cotransfected into *E. coli* strain JM101, where they were maintained by ampicillin and kanamycin selection. [$^3$H] Myristate was used to label cultures of logarithmically growing cells during sequential expression of yeast NMT1 followed by Cα. Lysates prepared from the cultures were subjected to SDS-PAGE and fluorography to examine radiolabeled fatty acid incorporation into protein. When the NMT1 and wild type Cα sequences were coexpressed in *E. coli*, a 40 kDa protein was metabolically labeled after addition of [$^3$H]myristic acid to the culture medium (lane 4 of FIG. 1B). This protein co-migrated with purified C-subunit standards. Labeling of the 40 kDa protein was absolutely dependent upon the presence of both NMT1 and wild type Cα. *E. coli* which expressed NMT1 but lacked Cα, and *E. coli* which lacked NMT1 but expressed Cα, each failed to label the 40 kDa protein with [$^3$H]fatty acid (lanes 6 and 7 of panel B, respectively). Moreover, the 40 kDa protein was not labeled in cells expressing NMT1 and the mutant Cα cDNA encoding the Ala$^2$ substituted C-subunit (lane 5 of panel B). Western blot analysis using rabbit polyclonal antisera raised against the C-subunit of mouse PK-A confirmed the presence of equivalent amounts of the Gly$^2$- and Ala$^2$-40 kDa proteins in lysates prepared from *E. coli* strain JM101 containing the wild-type and mutant Cα recombinant plasmids, respectively (FIG. 1E). The level of production of the two C-subunits was estimated to be 0.1% of total *E. coli* protein based on the signal intensities of purified C-subunit standards included in the Western blot. NMT represented approximately 0.2% of *E. coli* proteins after induction. This value was calculated from the NMT activities in crude lysates and the specific activity of purified yeast NMT [Towler et al., *Proc. Natl. Acad. Sci. USA* 84, 2708–2712 (1987)]. Co-expression of NMT1 and Cα had no deleterious effects on *E. coli* growth kinetics during the induction period.

The [$^3$H]myristate labeled 40 kDa protein was excised from an SDS-polyacrylamide gel and digested with Pronase E to investigate the nature of the fatty acyl-protein linkage. A labeled product was produced which co-migrated with the chemically synthesized [$^3$H]myristoylglycine standard [Towler and Glaser, *Biochemistry* 25, 878–884 (1986)] on C$_{18}$ reverse-phase high performance liquid chromatography (HPLC) [Heuckeroth and Gordon, *Proc. Natl. Acad. Sci. USA* 86, 5262–5266 (1989)]. Together these data supported the conclusion that (i) the C-subunit of PK-A can be myristoylated in a Gly$^2$ dependent manner only in *E. coli* cells producing yeast NMT, and (ii) that the endogenous methionylaminopeptidase activity of *E. coli* [Sherman et al., *BioEssays* 3, 27–31 (1985)] can remove the initiator Met of the C-subunit, thereby exposing its Gly$^2$ residue for NMT-catalyzed transfer of myristate. This latter result confirms earlier results identifying the NH$_2$-terminal sequence of the C-subunit synthesized in *E. coli* as Gly-Asn-Ala-Ala . . . (Slice and Taylor, supra.).

It was estimated that the overall efficiency of NMT-catalyzed linkage of the myristoyl moiety to the C-subunit in *E. coli* was virtually 100% by measuring the following three parameters: (1) the concentration of C-subunit in *E. coli* lysates from Western blot hybridization analysis; (2) the amount of [$^3$H]-myristate incorporated into the protein after excising bands from SDS-polyacrylamide gels containing a known amount of *E. coli* lysate proteins; and (3) the final specific activity of [$^3$H]-myristic acid in *E. coli*$^2$ after labeling (13 μmCi/nmol) [Silbert et al., *Biochemistry* 12, 164–171 (1973)].

Reconstitution of Protein N-myristoylation in *E. coli* is Specific for 14 Carbon Fatty Acids. 10 -(Propoxy)decanoic acid (11-oxamyristic acid) is an analog of myristic acid that has a similar chain length but a reduced hydrophobicity (comparable to decanoic acid) due to the substitution of an oxygen atom for a methylene group at position 11 of the hydrocarbon chain [Heuckeroth et al., *Proc. Natl. Acad. Sci. USA* 85, 8795–8799 (1988)]. When 11-oxamyristate is incorporated into p60$^{v\text{-}src}$ in vivo, it causes a significant redistribution of the protein from membrane to cytosolic fractions [Heuckeroth et al., *Proc. Natl. Acad. Sci. USA* 86, 5262–5266 (1989)]. Metabolic labeling tests analogous to those described above with [$^3$H]myristic acid, indicated that the C-subunit could also be labeled in a Gly$^2$ dependent manner when exogenous [$^3$H]11-oxamyristate or [$^3$H]palmitate was added to NMT producing *E. coli* cells (panels D and C in FIG. 1, respectively). Previous studies have suggested that palmitate must be metabolically converted to myristate before incorporation into N-myristoyl proteins [Heuckeroth et al., *Proc. Natl. Acad. Sci. USA* 85, 8795–8799 (1988); Towler and Glaser, *Biochemistry* 25, 878–884 (1980); Olson et al., *J. Biol. Chem.* 260, 3784–3790 (1984)]. Pronase E digestion of the [$^3$H]palmitate-labeled C-subunit yielded a product that co-migrated on C$_{18}$ reverse-phase HPLC with [$^3$H]myristoylglycine. Thus, the coupled *E. coli* expression recapitulates the remarkable specificity for fatty acyl-CoA chain length observed in *S. cerevisiae* and mammalian cells.

At least two proteins of about 45 and 55 kDa incorporated all three exogenously added [$^3$H]fatty acids in *E. coli* strains that expressed yeast NMT (lanes 3–6 in panels B-D of FIG. 1). Cells without plasmids (lane 1) or cells carrying the parental vector lacking NMT1. (lane 2) did not incorporate label into these proteins. Since the apparent M$_r$ of these proteins is conspicuously similar to the two forms of NMT produced in *E. coli*, the nature of the protein-[$^3$H]fatty acid association was investigated. Pronase E digestion of these proteins labeled with either [$^3$H]myristate or [$^3$H]palmitate yielded a product that co-migrated with [$^3$H]myristoylglycine on C$_{18}$ reverse-phase HPLC. The fact that myristoylglycine was detected, together with the observation that neither intact yeast NMT nor its proteolytically processed 45 kDa form contains a Gly at its NH$_2$-terminus, supported the conclusion that these [$^3$H]proteins do not arise from N-myristoylation of NMT itself but rather from N-myristoylation of endogenous *E. coli* proteins. One cannot, however, eliminate the possibility that a portion of the band intensities arises from a tight, noncovalent association of the [$^3$H]fatty acids with NMT species. A search [Towler et al., *J. Biol. Chem.* 263, 1784–1790 (1988); Devereux et al., *Nuc. Acids Res.* 12, 387–395 (1984)] of the NBRF protein database (Release 19.0) for *E. coli* protein sequences that begin with MetGly . . . and therefore might be acylated by NMT, did not reveal any of the appropriate molecular weight. Even with these two "endogenous" protein substrates, a major advantage of the bacterial system over eukaryotic systems is the absence of both endogenous NMT activity and substrates. The testing of alternative substrates for NMT such as heteroatom-containing analogs now becomes much more straightforward than in eukaryotic cells.

TABLE I

Peptide and Acyl-CoA Substrate Specificities of E. coli-derived S. cerevisiae NMT

| | Total E. coli NMT $K_m(\mu M)$ $V_{max}$ | | 45 kDa E. coli NMT $K_m(\mu M)$ $V_{max}$ | | Yeast NMT $K_m(\mu M)$ $V_{max}$ | |
|---|---|---|---|---|---|---|
| Peptide Substrate: | | | | | | |
| GNAAAARR | 65.8 | 100% | 62.5 | 100% | 60 | 100% |
| GNAASARR | 0.103 | 3.6% | 0.38 | 4.9% | 0.1 | 3% |
| GSAAAARR | 697 | 27.6% | ND | | 1700 | 50% |
| GSAASARR | 2.1 | 29% | ND | | 3.0 | 34% |
| GSSKSKPK | 48.5 | 33% | 66 | 52% | 40 | 43% |
| GPAAAARR | 7100 | 21.6% | — | <2% | — | <2% |
| GNAADARR | 503 | 4.9% | — | <2% | — | <2% |
| GDAAAARR | 645 | 4.2% | — | <2% | — | <2% |
| ANAAAARR | Not a substrate | | Not a substrate | | Not a substrate | |
| MGNAAAARR | Not a substrate | | Not a substrate | | Not a substrate | |
| GYAAAARR | — | <2% | — | <2% | Not a substrate | |
| ASSKSKPK | Not a substrate | | Not a substrate | | Not a substrate | |
| Fatty Acid Substrates: | | | | | | |
| Myristoyl-CoA | ND | | 0.36 | 100% | 0.675 | 100% |
| Palmitoyl-CoA | ND | | 0.96 | 22.4% | 0.700 | 21% |
| 11-oxamyristoyl-CoA | ND | | 1.2 | 450% | 6.1 | 270% |

The peptide $K_m$ and $V_{max}$ values shown in the above Table I are averages obtained from 4- or 5-point Lineweaver-Burke plots. These plots were produced using data generated in at least three independent in vitro NMT assays. Varying concentrations of peptides were assayed with 15 μM myristate to determine peptide $K_m$ and $V_{max}$ values. Fatty acyl-CoA $K_m$ and $V_{max}$ values were obtained in a similar manner except varying concentrations of fatty acid were used with 60 μM GNAAAARR (i.e. peptide at its $K_m$ concentration). Yeast NMT was from a 570 fold purified preparation [Towler et al., Proc. Natl. Acad. Sci. USA 84, 2708–2712 (1987)]. Synthetic peptide substrates are represented by their conventional one letter amino acid code. $V_{max}$ values are percentages of those obtained when GNAAAARR and myristoyl-CoA were used as the peptide and acyl-CoA substrates, respectively. ( - - - ) indicates that the quantity of enzyme needed to accurately determine the $K_m$ was prohibitively large. Peptides labeled "not a substrate" had $V_{max} < 1\%$. ND=not determined.

Various other examples will be apparent to the person skilled in the art after reading the present disclosure without departing from the spirit and scope of the invention. It is intended that all such other examples be included within the scope of the appended claims.

What is claimed is:
1. Plasmid pBB131.
2. Plasmid pBB132.
3. Plasmid pBB133.
4. Plasmid pBB125.

* * * * *

UNITED STATES PATENT OFFICE
CERTIFICATE OF CORRECTION

PATENT NO. : 5,504,008
DATED : APRIL 2, 1996
INVENTOR(S) : ROBERT J. DURONIO, et al.

It is certified that error appears in the above—identified patent and that said Letters Patent is hereby corrected as shown below:

At col. 1, line 6, the following acknowledgment of government support should be entered after the cross-reference paragraph:

"This invention was made in part with government support under Grant number AI 27179, awarded by the National Institutes of Health. The government has certain rights in the invention."

Signed and Sealed this

Seventh Day of January, 1997

Attest:

BRUCE LEHMAN

Attesting Officer

Commissioner of Patents and Trademarks